United States Patent [19]
Cortes

[11] Patent Number: 6,067,664
[45] Date of Patent: May 30, 2000

[54] COMBINED EAR AND EYE PROTECTION DEVICE

[76] Inventor: Luis Cortes, 1515 W. 9th St., Santa Ana, Calif. 92703-2933

[21] Appl. No.: 09/321,754

[22] Filed: May 28, 1999

[51] Int. Cl.[7] ............................................. A61F 9/02
[52] U.S. Cl. ...................................... 2/431; 2/209; 2/452
[58] Field of Search .............................. 2/431, 432, 452, 2/209; 351/158, 123; 128/857, 864, 867, 868

[56]      References Cited

U.S. PATENT DOCUMENTS

| 4,683,587 | 7/1987 | Silverman | 351/158 X |
|---|---|---|---|
| 5,278,999 | 1/1994 | Brown et al. | 2/209 |
| 5,475,449 | 12/1995 | Pyle | 351/123 |
| 5,541,677 | 7/1996 | Huhtala | 351/156 |
| 5,619,750 | 4/1997 | Allewalt | 2/13 |
| 5,715,323 | 2/1998 | Walker | 351/123 X |
| 5,717,479 | 2/1998 | Rickards | 351/158 |
| 5,718,002 | 2/1998 | Pavlak | 2/243 |

*Primary Examiner*—Peter Nerbun
*Attorney, Agent, or Firm*—Goldstein & Canino

[57]      ABSTRACT

An ear and eye protection device for allowing a user to protect his eyes and ears simultaneously from the elements. The device comprises an eyewear having a right side and a left side, a pair of temple stems extending backward from the right side and the left side of the eyewear, and a pair of earplugs slidably mounted from the eyewear, such that the earplugs may be pulled downward towards the user's ears. According to the preferred embodiment, the earplugs may be secured to the free ends of the temple stems when the earplugs are not in use.

8 Claims, 2 Drawing Sheets

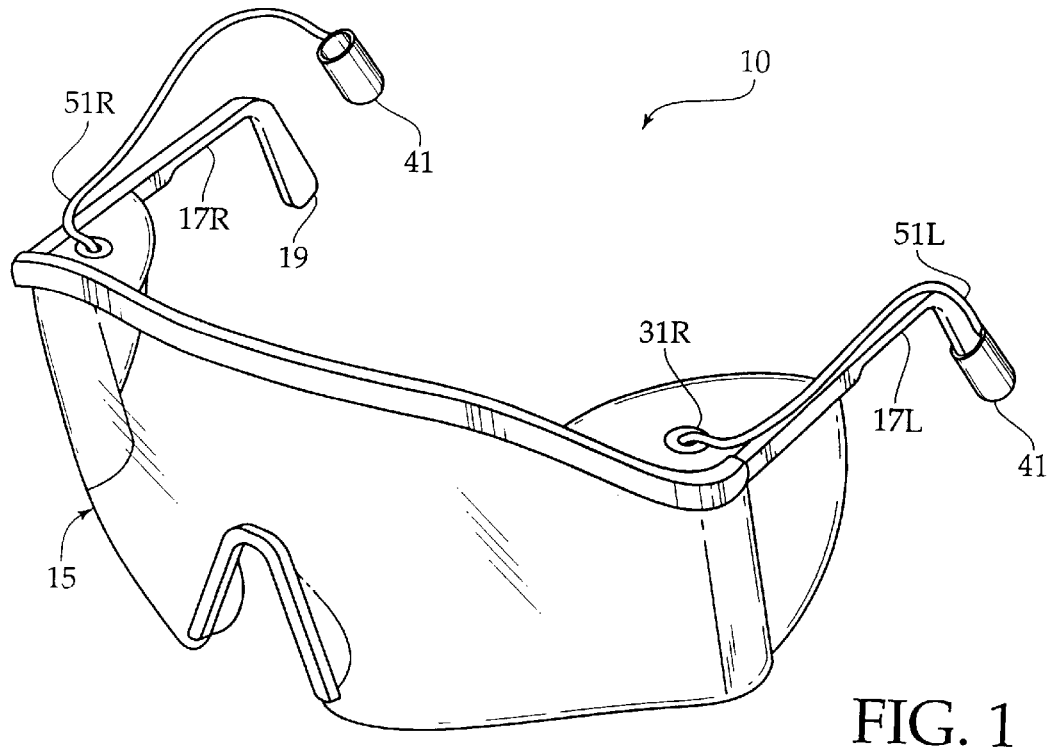
FIG. 1
FIG. 2
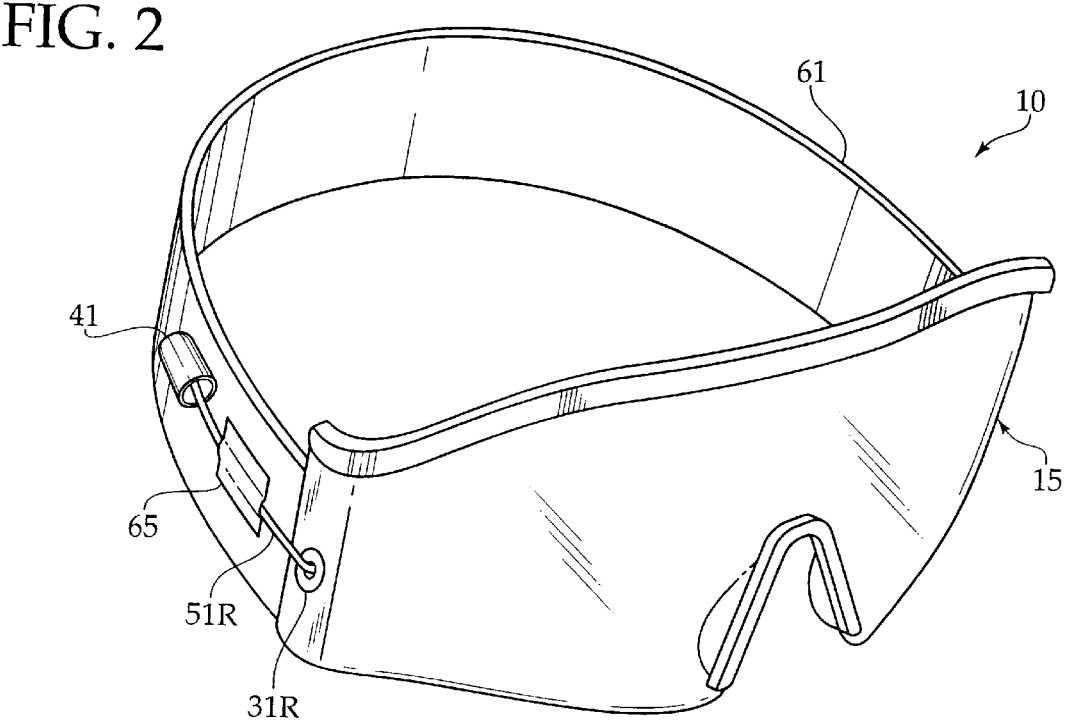

COMBINED EAR AND EYE PROTECTION DEVICE

FIELD OF THE INVENTION

The invention relates to an ear and eye protection device. More particularly, the invention relates to a compact apparatus that allows wearers to protect their eyes and ears simultaneously.

BACKGROUND OF THE INVENTION

Protective eyewear have been worn for various different applications. Primarily, protective eyewear has been used for protection in various sports as well as for protection by workmen engaged in occupations with exposure to dangerous conditions. In particular, protective eyewear has been used in high speed sports such as motorcross, skiing and skydiving; contact sports such as basketball, hockey and football; and sports involving a fast-moving projectile such as racket ball, splat-ball and squash. Not only does such eyegear protect one's eyes against contact with foreign objects, but also prevents eye strain that may result from exposure to elements such as sun's glare or the blowing winds.

Protective eyegear is also highly desirable and often used while engaging in under-water activities, such as diving, snorkeling or the like, for preventing water from entering into one's eyes. Unfortunately, these conventional eye protection devices fail to prevent water from entering into one's ears.

Some efforts have been made to develop devices that enable one to protect their eyes and ears simultaneously. For example, U.S. Pat. No. 5,718,002 to Pavlak discloses a device that comprises a pair of reading glasses and a pair of wind-deflecting deflectors to prevent air from entering into ones ears. Likewise, U.S. Pat. No. 5,619,750 to Allewalt discloses an apparatus which includes eye glasses with attached nose shields, side shields and ear shields. Unfortunately, while these protective devices protect ones ears from blowing wind, they fail to prevent water from entering into the wearer's ears when the protective device is used under water.

While the prior art devices may be suitable for the particular purpose employed, or for general usage, they would not be as suitable for the purposes of the present invention as disclosed hereinafter.

SUMMARY OF THE INVENTION

It is an object of the present invention to provide an ear and eye protection device.

It is another object of the present invention to provide a compact apparatus that allows wearers to protect their eyes and ears simultaneously. Accordingly, herein is disclosed an ear and eye protection device that comprises an eyewear and a pair of ear plugs that are securely mounted from the eyewear. The ear plugs can be extended downward to allow insertion thereof into the wearer's ears.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims and their legal equivalents.

BRIEF DESCRIPTION OF THE DRAWINGS

The above and other aspects, features and advantages of the present invention will be more apparent from the following detailed description thereof, which is presented in conjunction with the following drawings, wherein corresponding reference characters indicate corresponding components throughout the drawing figures.

FIG. 1 is a diagrammatic perspective view of one embodiment of the present invention, showing the earplugs secured to the free ends of the temple bars.

FIG. 2 is a diagrammatic perspective view of a second embodiment, wherein the earplugs are secured on the outer surface of a headband when not in use.

DETAILED DESCRIPTION OF THE PREFERRED EMBODIMENTS

Figure 3:
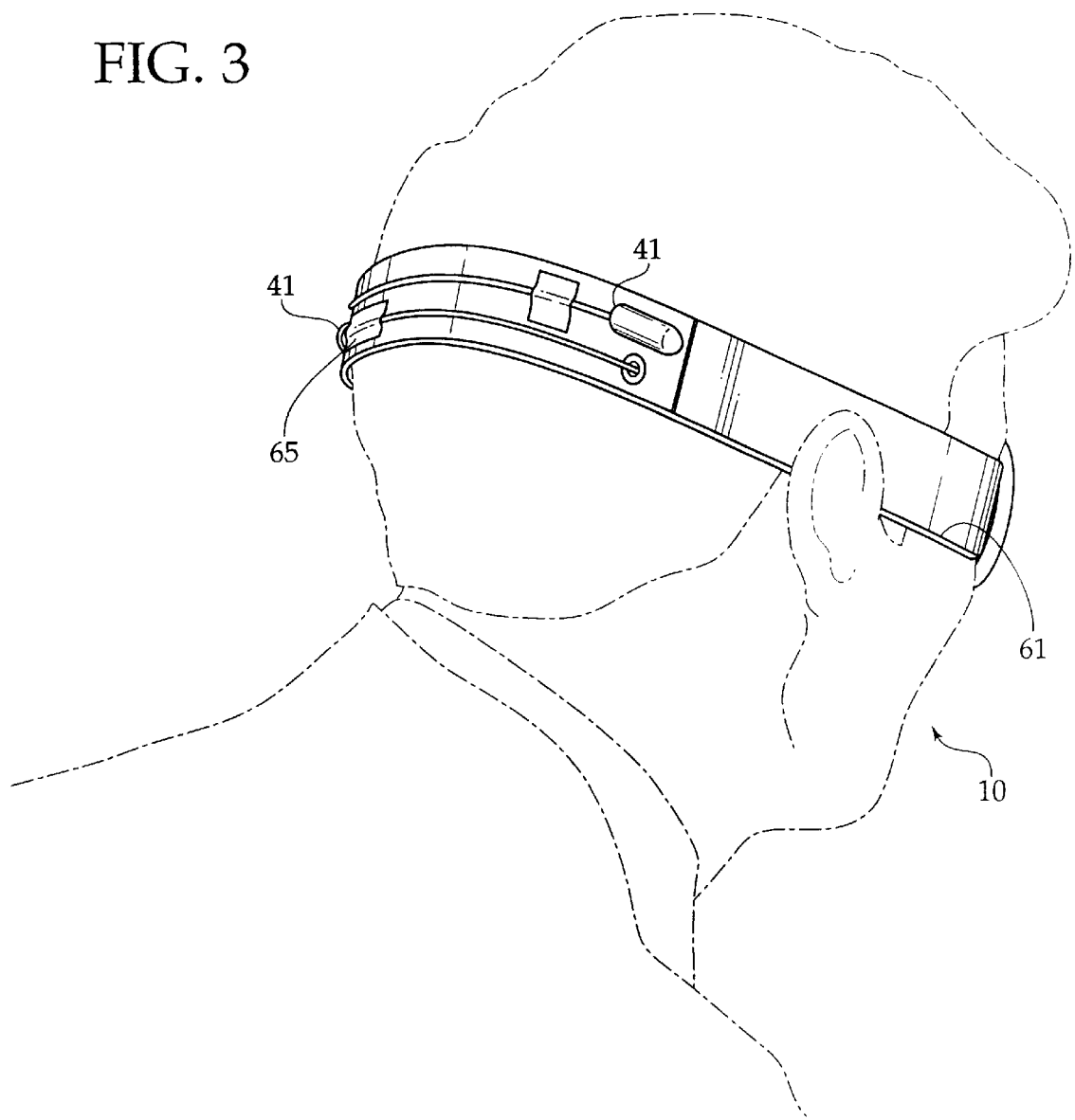
FIG. 3 is a diagrammatic perspective view of another embodiment, wherein the earplugs are secured towards the rear of the headband when not in use.

FIGS. 1–3 relate to an ear and eye protection device 10 that allows users to shield their eyes as well as use an earplug simultaneously for shielding one's ears from external noise or the like.

As shown in FIG. 1, the ear and eye protection device 10 comprises an eyewear 15. According to the invention, the eyewear 15 can be provided in different variations so that it is adaptable for different uses. Thus, it is possible to selectively design and construct the eyewear 15 as a sun glass, a prescription glass, a swimming goggle, a scuba diving goggle or the like. It is preferable that the eyewear 15 be shatterproof to allow rough usage thereof.

The eyewear 15 has a right side and a left side, wherein the right side has a right temple stem 17r and the left side has a left temple stem 17l extending therefrom. Each of the two temple stems 17r, 17l has a free end 19 that lies opposite from the end extending from the eyewear 15.

According to the invention, the ear and eye protection device 10 is provided with a pair of earplugs 41. As is well known, the user typically uses the earplugs 41 for shielding his ears from external noise or from water when the user is under water. The earplugs 41 are partially inserted into the ears so that the earplug 41 blocks noise, water or the like from entering the ears. The partial insertion of the earplugs 41 allows them to be easily removed from the ears when the user no longer needs them.

According to the preferred embodiment as shown in FIG. 1, the ear and eye protection device 10 has a right hole 31r and a left hole (not shown) on the right and left sides of the eyewear 15, adjacent to the right and left temple stems 17r, 17l extending therefrom.

The ear and eye protection device 10 is provided with a right wire 51r and a left wire 51l, each of which securely attaches the earplugs 41 thereto. The right wire 51r is slidably mounted from the right hole 31r and the left wire 51l is slidably mounted from the left hole, which ensures that the wires 51r, 51l may be slid outward therefrom. Preferably, the wires 51r, 51l are constructed from a sturdy material and are rigid in structure.

The eyewear 15 has a wire housing with the right hole 31r and the left hole providing openings thereto. As a result, the wires 51r, 51l may be pushed into the wire housing from the right and left holes when the earplugs 41 are not in use. The wire housing is internally hollow to allow easy storage of the wires 51r, 51l mounted therein.

According to the preferred embodiment, when the earplugs 41 are not in use, they are secured to the free end 19 so that the earplugs appear to be part of the temple stems 17r, 17l, thus providing an aesthetically pleasing look thereto.

According to the invention, the user puts on the ear and eye protection device 10 by placing the temple stems 17r, 17l over their ears, such that the ear and eye protection device 10 rests in front of the user's eyes similar to typical eye glasses. The earplugs 41 are taken off of the free end 19 of the temple stems 17r, 17l and pulled downward and inserted into the left and right ears. It is envisioned that the earplugs 41 are pulled towards the ears, the wires 51r, 51l end up sliding out of the holes 31r, 31l. On the other hand, when the earplugs 41 are no longer needed for use, the wires are slid back into the holes 31r, 31l, such that a portion of the wires are housed within the wire housing and the earplugs 41 are fitted onto the free ends 19.

According to a second embodiment, as shown in FIG. 2, the ear and eye protection device 10 is provided with a headband 61 that fits around a user's head. The headband 61 has a pair of earplug securement sleeves 65 on its left and right surfaces. The earplug securement sleeves 65 securely hold the wires 51r, 51l therein when the earplugs 41 are not in use, which ensures that the earplugs remain tightly fastened to the headband 61 and do not droop downward.

It should be noted that the scope of the present invention is not limited by the exact location of the holes 31r, 31l and the earplug securement sleeves 65. Accordingly, it is possible to provide the holes 31r, 31l and the earplug securement sleeves 65 towards the back of the headband 61 as shown in FIG. 3, such that the earplugs 41 lie directly opposite from the eyewear 15. According to this embodiment, the wire housing is located towards the rear of the headband 61.

In summary, herein is disclosed an ear and eye protection device 10, which comprises an eyewear and a pair of ear plugs that are slidably mounted from the eyewear. The earplugs may be selectively pulled downward towards the user's ears to allow use of the eyewear and the earplugs simultaneously.

Many specific details contained in the above description merely illustrate some preferred embodiments and should not be construed as a limitation on the scope of the invention. Accordingly, many other variations are possible within the spirit of the present invention, limited only by the scope of the appended claims.

What is claimed is:

1. An ear and eye protection device for allowing a user to protect his eyes and ears from the elements, comprising:

an eyewear having a right side and a left side;

a pair of temple stems extending backward from the right side and the left side of said eyewear, said temple stems having a free end opposite from said eyewear;

a pair of earplugs slidably mounted from said eyewear, such that the earplugs may be pulled downward towards the user's ears;

a wire housing within the eyewear; and a pair of wires slidably mounted from said wire housing, said wires securely attaching said earplugs thereto.

2. The ear and eye protection device of claim 1, wherein said wire housing is provided with a left hole and a right hole, such that said wires extend into the wire housing from the left hole and the right hole.

3. The ear and eye protection device of claim 2, wherein said earplugs may be secured to said free ends of the temple stems when the earplugs are not in use.

4. An ear and eye protection device for allowing a user to protect his eyes and ears from the elements, comprising:

an eyewear having a right side and a left side;

a headband mounted to the right side and the left side of said eyewear, said headband having a left surface, a right surface and a rear surface; and a pair of earplugs slidably mounted from said eyewear, such that the earplugs may be pulled downward towards the user's ears.

5. The ear and eye protection device of claim 4, further comprising:

a wire housing within the eyewear; and a pair of wires slidably mounted from said wire housing, said wires securely attaching said earplugs thereto.

6. The ear and eye protection device of claim 5, wherein the headband has a pair of securement sleeves on the left and the right surface, said securement sleeves securely holding said wires therein when said earplugs are not in use to ensure that said earplugs remain tightly secured to said headband.

7. The ear and eye protection device of claim 4, further comprising:

a wire housing located within the rear surface of said headband; and a pair of wires slidably mounted from said wire housing, said wires securely attaching said earplugs thereto.

8. The ear and eye protection device of claim 7, wherein the headband has a pair of securement sleeves on the rear surface, said securement sleeves securely holding said wires therein when said earplugs are not in use to ensure that said earplugs remain tightly secured to said headband.

* * * * *